United States Patent [19]

Veber et al.

[11] Patent Number: 4,680,283
[45] Date of Patent: Jul. 14, 1987

[54] ANALOGS OF SUBSTANCE P AND ELEDOISIN

[75] Inventors: Daniel F. Veber, Ambler; Roger Freidinger, Hatfield, both of Pa.

[73] Assignee: Merck & Co., Inc., Rahway, N.J.

[21] Appl. No.: 898,274

[22] Filed: Aug. 20, 1986

Related U.S. Application Data

[63] Continuation-in-part of Ser. No. 852,479, Apr. 16, 1986, which is a continuation of Ser. No. 654,432, Sep. 26, 1984.

[51] Int. Cl.$^4$ .................. A61K 37/02; C07K 7/02; C07K 5/08; C07K 5/10
[52] U.S. Cl. ........................................ 514/17; 514/18; 530/332; 530/331; 530/330
[58] Field of Search ............... 530/329, 800, 330, 331, 530/332; 514/17, 18

[56] References Cited

U.S. PATENT DOCUMENTS 4,472,305  9/1984  Hansen et al. ..................... 530/329

OTHER PUBLICATIONS

DeCastiglione, Exploitation and Exploration of Ceruletide and Eledoisin, Biopolymers, 22, 507–515, (1983).
Sandberg & Iversen, Substance P, J. Med. Chem., 25, 1009, (1982).
Laufer et al., Persistent Action of N-methylated Analogs of Substance P on Rat Parotid Slices, FEBS. Letters, 123, 291, (1981).
Friedinger et al., Bioactive Conformation of Luteinizing Hormone-Releasing Hormone, Science, 210, 656–658, (1980).
The Peptides, vol. II, pp. 137–153, Synthesis, Occurence and Action of Biologically Active Polypeptides, Ed. E. Schroder & K. Lubke, (Academic Press, N.Y., 1966).
Freidinger et al., Protected Lactam-Bridged Dipeptides for Use as Conformational Constraints in Peptides, J. Org. Chem., 47, 104, (1982).
Substance P Metabolism & Biological Action, Piercey et al., ed. Jordan & Oehme, (London), 1985, (pp. 165–176).

*Primary Examiner*—Delbert R. Phillips
*Attorney, Agent, or Firm*—William H. Nicholson; Michael C. Sudol

[57] ABSTRACT

Analogs of substance P and eledoisin which are conformationally constrained by the presence of a lactam in the peptide chain demonstrate greater selectivity and increased protease stability and are useful as analgesic, anti-inflammatory, antihypertensive, central nervous system agents, and stimulants of lachrymal secretion. The compounds are prepared by standard peptide synthetic procedures.

12 Claims, No Drawings

ANALOGS OF SUBSTANCE P AND ELEDOISIN

This is a continuation-in-part of copending application Ser. No. 852,479 filed Apr. 16, 1986 which in turn is a continuation of application Ser. No. 654,432, filed Sept. 26, 1984.

SUMMARY OF THE INVENTION

Analogs of substance P and eledoisin with general structural formula:

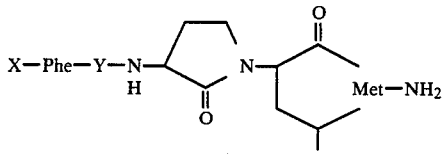

are useful in the treatment of dry eye syndrome by stimulation of lachrymal secretion. They also demonstrate analgesic, anti-inflammatory, hypotensive and CNS activity.

BACKGROUND OF THE INVENTION

Substance P and eledoisin are naturally occurring undecapeptides belonging to the tachykinin family of peptides so named because of their prompt stimulatory action on smooth muscle. Eledoisin was originally isolated from the posterior salivary glands of the Mediterranean octopod *Eledone moschata*. A mammalian tachykinin is substance P, a neuropeptide originally isolated from gut. These peptides have the following amino acid sequences:

Glu—Pro—Ser—Lys—Asp—Ala—Phe—

—Ile—Gly—Leu—Met—NH$_2$
(eledoisin)

```
          6    7
Arg—Pro—Lys—Pro—Gln—Gln—Phe—

8    9   10   11
         —Phe—Gly—Leu—Met—NH2
              (substance P)
```

These materials suffer the typical shortcomings of pharmacologically active peptides such as susceptibility to enzymatic degradation and lack of pharmacological specificity which severely limit their use as therapeutic agents. Modification by incorporation of D-amino acids and/or N-methyl amino acids and shortening of the peptides to six amino acids has produced compounds with enhanced metabolic stability (Sandberg et al., *J. Med. Chem.*, 25, 1009 (1982); The Peptides, Vol. II, Schroder and Lübke, Eds., pp. 137-152 (1966)).

The shortest active sequence demonstrating eledoisin activity and selectivity has been

```
   6    7   8    9   10   11
  Glu—Phe—Phe—Gly—Leu—Met—NH2
``` which corresponds to the last six amino acids of substance P.

Another technique which has been employed for altering the pharmacological and biochemical properties of peptides comprises the introduction of conformational constraints imposed by formation of relatively rigid ring systems within the peptide chains (Freidinger et al., *Science*, 210, 656-658 (1980); Freidinger et al., *J. Org. Chem.*, 47, 104 (1982)).

Now, with this invention there are provided peptides related to substance P and eledoisin with increased activity, increased selectivity for eledoisin receptors and increased resistance to protease degradation through the use of lactam conformational constraints, optionally in combination with other methods of peptide modification.

In the specification and claims hereof the following abbreviations are employed:

| | | |
|---|---|---|
| <Glu | Pyroglutamic acid | $\begin{array}{c}H\\|\\N\end{array}$—COOH, O= |
| Pro | Proline | $\begin{array}{c}H\\|\\N\end{array}$—COOH |
| Ser | Serine | H$_2$N—CH—COOH<br>            \|<br>           CH$_2$OH |
| Lys | Lysine | H$_2$N—CH—COOH<br>            \|<br>         (CH$_2$)$_4$NH$_2$ |
| Asp | Aspartic acid | H$_2$N—CH—COOH<br>            \|<br>         CH$_2$COOH |
| Ala | Alanine | H$_2$N—CH—COOH<br>            \|<br>         CH$_3$ |
| Phe | Phenylalanine | H$_2$N—CH—COOH<br>            \|<br>         CH$_2$—C$_6$H$_5$ |
| N—Me—Phe | N—methyl phenylalanine | CH$_3$<br>\|<br>HN—CH—COOH<br>     \|<br>    CH$_2$—C$_6$H$_5$ |
| Ile | Isoleucine | H$_2$N—CH—COOH<br>            \|<br>         CH—CH$_3$<br>          \|<br>        CH$_2$CH$_3$ |
| Gly | Glycine | H$_2$N—CH$_2$—COOH |
| Leu | Leucine | H$_2$N—CH—COOH<br>            \|<br>         CH$_2$<br>         \|<br>       CH(CH$_3$)$_2$ |
| Met | Methionine | H$_2$N—CH—COOH<br>            \|<br>         CH$_2$<br>         \|<br>        CH$_2$SCH$_3$ |
| Arg | Arginine | H$_2$N—CH—COOH<br>            \|<br>         CH$_2$<br>         \|<br>        CH$_2$     NH<br>         \|       \|\|<br>       CH$_2$—NH—C  NH$_2$ |

| | | |
|---|---|---|
| Gln | Glutamine | H₂N—CH—COOH<br>          │<br>          CH₂<br>          │<br>          CH₂CONH₂ |
| Ac—Ala | Acetylalanine | $CH_3C(O)-NH-CH(CH_3)-COOH$ |
| Ac—Phe | Acetylphenyl-alanine | $CH_3C(O)-NH-CH(CH_2C_6H_5)-COOH$ |
| Tyr | Tyrosine | $H_2N-CH(CH_2C_6H_4OH)-COOH$ |
| Val | Valine | $H_2N-CH(CH(CH_3)_2)-COOH$ |

DETAILED DESCRIPTION OF THE INVENTION

The novel compound of this invention has structural formula I:

X—Phe—Y—NH—[lactam]—Met—NH₂ wherein: X is <Glu, <Glu-Gln, Ac-Ala, Ac-Phe or Ac; and Y is Phe, N-Me-Phe, Ile, Val, or Tyr.

It is preferred that X be pyroglutamic acid. It is also preferred that Y be phenylalanine, isoleucine or valine, and most preferably phenylalanine.

It is further preferred that the asymmetric carbon (*) in formula I provides the D or (R)-enantiomer.

The novel compounds of this invention are prepared in the most part by standard peptide syntheses. However, the novel key intermediate lactam is prepared by a novel process comprising cyclo-alkylation of an amide nitrogen with methionine methylsulfonium iodide, and may be depicted as follows:

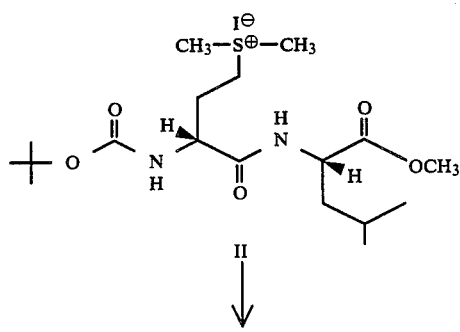

II

↓

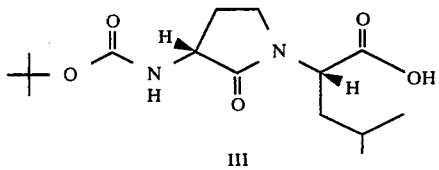

III

The reaction is conducted in an inert organic solvent such as DMF, HMPA, DMSO or the like admixed with a chlorinated hydrocarbon such as chloroform, methylene chloride, ethylene dichloride or the mixtures thereof, preferably a DMF/CH₂Cl₂ mixture and preferably a 1:1 (v/v) mixture by treatment of compound II with a strong base such as an alkali metal hydride, especially sodium hydride or an alkali metal organic compound such as phenyl lithium, n-butyl lithium or the like at about −20° C. to +10° C., preferably about 0° C. for about 1 to 6 hours, preferably about 2 hours. The reaction is preferably conducted in an inert atmosphere such as under nitrogen or argon.

As mentioned previously the compound II is prepared by standard peptide syntheses and treatment with methyl iodide for about 48 hours. Similarly the various 6-membered peptide analogs comprised by structural formula I are synthesized by further peptide procedures.

For use as a stimulant of lachrymal secretion the novel compound of this invention is applied as a topical ophthalmic formulation which may be in the form of a solution, suspension, emulsion, ointment, or solid ophthalmic insert the carrier device for which may be non-biodegradable, biodegradable, or simply soluble in lachrymal fluids.

The ophthalmological preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000; 1,500; 4,000; 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenylethanol, buffering ingredients such as sodium chloride, sodium borate, sodium acetate, gluconate buffers, and other conventional ingredients such as sorbitan monolaurate, triethanolamine, polyoxyethylene sorbitan monopalmitate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lachrymal fluids, or otherwise disintegrates.

In the novel method of treatment of this invention an effective lachrymal secretion stimulatory amount is about 0.01 to about 5 mg per day per eye, and preferably about 0.1 to 0.5 mg per day per eye, as a single dose or a 2 to 4 doses per day regimen.

For use as an analgesic, anti-inflammatory, antihypertensive or centrally active agent, the novel compound of this invention, is administered systemically such as by injection, rectally, intranasally, or orally, preferably the latter in a unit dosage form designed for the particular route of administration. Systemic doses of about 0.1 to 25 mg per kilogram per day are satisfactory, administered on a 1 to 4 times a day regimen.

EXAMPLE 1

Pyroglutamyl-ohenylalanyl-phenylalanyl-[(R)-3-amino-2-oxo-1-pyrrolidine-(S)-4-methyl-2-Pentanoyl]methionine amide Step A: Preparation of tert-Butyloxycarbonyl-D-methionyl-L-leucine methylester Boc-D-methionine (34.2 g, 0.137 mole) and L-leucine methylester hydrochloride (25.0 g, 0.137 mole) was dissolved in 450 ml of methylene chloride and triethylamine (19.15 ml, 13.9 g, 0.137 mole) was added. Dicyclohexylcarbodiimide (62 ml of a 0.5 g/ml solution in $CH_2Cl_2$, 0.15 mole) was then added followed by stirring at room temperature overnight. The mixture was filtered and the filtrate was extracted with three 150 ml portions of dilute citric acid and three 150 ml portions of 1N sodium biocarbonate. After drying with sodium sulfate, the solution was concentrated in vacuo. Chromatography of the crude material on silica gel eluting with ethyl acetate-hexane (1:1; 2:1) followed by ethyl acetate gave pure product which crystallized from ethyl acetate-hexane to give 28.4 g of product (53%), m.p. 61°-64°. The nmr spectrum was consistent with the expected structure.

Step B: Preparation of tert-Butyloxycarbonyl-D-methionyl-L-leucine methylester methylsulfoniumiodide Boc-D-Met-Leu-OCH$_3$ (25 g, 66.5 mmol) was dissolved in methyl iodide (132 ml) and stirred at room temperature for 2 days. Concentration in vacuo gave 35.4 g (103%) of the sulfonium salt. The nmr spectrum was consistent with the proposed structure.

Step C: Preparation of (R)-3-[tert-Butyloxycarbonyl)amino]-2-oxo-1-pyrrolidine-(S)-4-methyl-2-pentanoic acid Boc-D-Met-Leu-OCH$_3$ methylsulfonium iodide (17.15 g, 33.2 mmol) was dissolved in 665 ml of 1:1 dimethylformamide-methylene chloride under nitrogen and cooled to 0° C. Sodium hydride (3.2 g of a 50% mineral oil suspension, 66.7 mmol) was then added in one portion and the mixture was stirred 2 hours at 0° C. Methyl acetate (220 ml) followed by water (3 ml) was added and the mixture was left to stand overnight at room temperature. The solution was concentrated to a small volume, and the residue was partitioned between methylene chloride and water. The water layer was acidified to pH 4 with concentrated citric acid and extracted three times with methylene chloride. The extracts were dried over sodium sulfate and concentrated in vacuo. The residue crystallized. Recrystallization from ethyl acetate-hexane gave 3.9 g (38%) of product, m.p. 162°-165°; $[\alpha]_D^{24} = +22.1°$, (c 1.0, CH$_3$OH). The nmr spectrum was consistent with the proposed structure.

Step D: Preparation of (R)-3-[tert-Butyloxycarbonyl)amino]-2-oxo-1-pyrrolidine-(S)-4-methyl-2-pentanoyl-(S)-methionine amide The protected lactam from Step C (1.19 g, 3.8 mmol) and methionine amide hydrochloride (0.77 g, 4.2 mmol) were dissolved in 225 ml of dimethylformamide and cooled to 5° C. Diphenylphosphorylazide (0.9 ml, 1.15 g, 4.2 mmol) and sodium bicarbonate (1.6 g, 15 mmol) were added, and the mixture was stirred for 2 days at 5° C. The mixture was concentrated in vacuo, and the residue was partitioned between ethyl actate and water. The ethyl acetate layer was washed with 2.5N citric acid (2×10 ml), water (10 ml), 0.5N potassium bicarbonate (2×12.5 ml), water (2×15 ml) and saturated aqueous sodium chloride solution (15 ml). The ethyl acetate solution was dried over MgSO$_4$, filtered, and concentrated in vacuo to a foam (1.57 g, 93%). The product showed a single major spot by tlc ($R_f$=0.84, silica gel, 30:5:1:1 ethyl acetate-pyridine-acetic acid-water) and was used without further purification.

Step E: Preparation (R)-3-amino-2-oxo-1-pyrrolidine-(S)-4-methyl-2-pentanoyl-(S)-methionine amide hydrochloride The protected tripeptide from Step D (1.5 g, 3.37 mmol) was dissolved in 50 ml of ethyl acetate and cooled to −30° C. under nitrogen. HCl gas was then bubbled through the solution rapidly while maintaining the temperature between −5° and 0° C. After saturation was reached, slow HCl addition was continued for 15 minutes. Nitrogen was then bubbled rapidly through the solution, and the cooling bath was removed. A gummy solid precipitated and the supernatant was decanted. The gummy solid was triturated with ethyl acetate (2×5 ml) followed by 1:1 ethyl acetate-hexane (10 ml) to give a solid which was filtered, and dried in vacuo giving 1.1 g (86%) of product; 1 major tlc spot, $R_f$=0.72 (silica gel, 80:20:2 chloroform-methanol-water.

Step F: Preparation of Pyroglutamyl-phenylalanyl-phenylalanine methylester

Pyroglutamyl-phenylalanyl-phenylalanyl-resin was prepared from Boc-phenylalanyl-resin (7 mmol) according to procedures described in Strachan et al., *J. Med. Chem.*, 22, 586 (1979). Amino acid analysis of the resin gave Glu, 0.99; Phe 2.01.

This resin was stirred in methanol (140 ml) containing triethylamine (14 ml) for 2 hours. Filtration and concentration of the filtrate in vacuo gave a viscous oil which crystallized on drying. Recrystallization from ethyl acetate-hexane gave 2.72 g (86%) of product. The nmr spectrum was consistent with the expected tripeptide ester. An additional treatment of the resin with triethylamine-methanol did not give significantly more product.

Step G: Preparation of Pyroglutamyl-phenylalanyl-phenylalanine hydrazide

To 14 ml of methanol cooled to 0° C. was added 7 ml of hydrazine, also cooled to 0° C. This solution was added rapidly to 2.04 g of ester prepared according to Step F. The resultant solution was stirred for 30 minutes at 0° C. followed by concentration in vacuo. The resultant oil was redissolved in methanol and reconcentrated 5 times to remove residual hydrazine and produce a negative Tollens test on tlc. The product weighed 2.05 g.

Step H: Preparation of Pyroglutamyl-phenylalanyl-phenylalanyl-[(R)-3-amino-2-oxo-1-pyrrolidine-(S)-4-methyl-2-pentanoyl]-methionine amide The hydrazide prepared according to Step G (0.84 g, 1.92 mmol) was dissolved in 17 ml of freshly degassed dimethylformamide and cooled to −20° C. A tetrahydrofuran solution of HCl (4.53 g HCl/25 ml of solution), 1.8 ml (9.15 mmol), was added maintaining the temperature below −8° C. The resultant solution was cooled to −25° C. and isoamyl nitrite (0.4 ml diluted to 4 ml with dimethylformamide) was added in increments until a positive starch/KI test for 30 minutes indicated complete conversion to acyl azide. A total of 2.9 ml of the isoamyl nitrite solution was required. One hour after completion of azide formation, the solution was cooled to −40° C. The tripeptide amine hydrochloride prepared according to Step E (0.766 g. 2.01 mmol in 4 ml of dimethylformamide) was then added, and the pH was adjusted to about 7.2 (according to moistened narrow range pH paper) with triethylamine (1.55 ml). The reaction mixture was kept at −20° C. for 23 hours with periodic adjustments of pH with triethylamine followed by 18 hours, at 5° C. At this point, coupling was complete by tlc, and the mixture was filtered and the filtrate was concentrated in vacuo. The residue was dissolved in 40 ml of 3:1 dimethylformamide-water (v/v) and stirred for 45 minutes with mixed bed resin (Bio-Rad AG 501-X8 (D)). The mixture was filtered, and the filtrate was concentrated in vacuo to 1.7 g of amorphous solid.

The crude product was chromatographed on silica gel eluting with 90:10:0.5:0.1 CHCl$_3$-MeOH-H$_2$O-acetic acid. The product containing fractions were combined and concentrated in vacuo to a solid, 0.452 g (31%). Amino acid analysis-Glu, 1.00; Phe, 1.97; Met, 1.02; HPLC, 97%; tlc, single spot in 3 systems; nmr spectrum consistent with expected structure.

Employing the procedures substantially as described in Example 1, there were produced the following compounds:

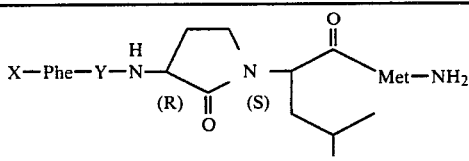

| Compound | X | Y |
| --- | --- | --- |
| L-363,851 | <Glu | Phe |
| L-363,232[1] | <Glu | Phe |
| L-653,547 | <Glu | Ile |
| L-653,561 | Ac—Phe | Val |
| L-653,562 | Ac—Ala | Ile |
| L-653,564 | <Glu | Val |
| L-653,563 | Ac | Ile |

[1] (S),(S)—

EXAMPLE 2

Pyroglutamyl-phenylalanyl-N-methyl-phenylalanyl-[(R)-3-amino-2-oxo-1-pyrrolidine-(S)-4-methyl-2-pentanoyl]methionine amide Using standard peptide synthetic procedures involving resin solid support techniques, as described by Sheppard et al. (1982) Proc. 8th American Peptide Symp., (Pierce Chemical Co., Rockford, Ill.) pp. 45–54, the subject compound was prepared by the following sequence of reactions, the product of which was characterized by mass spectrum, hplc, amino acid analysis and n.m.r.

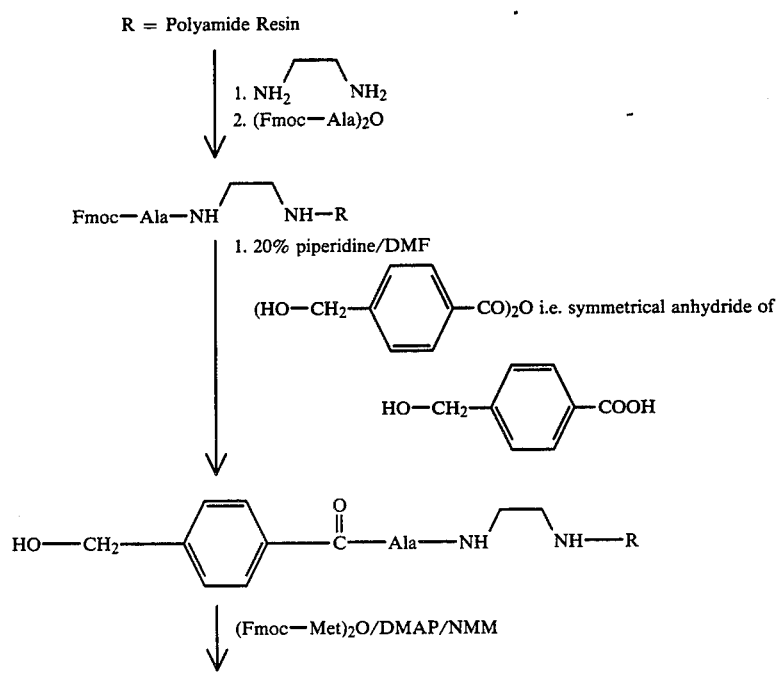

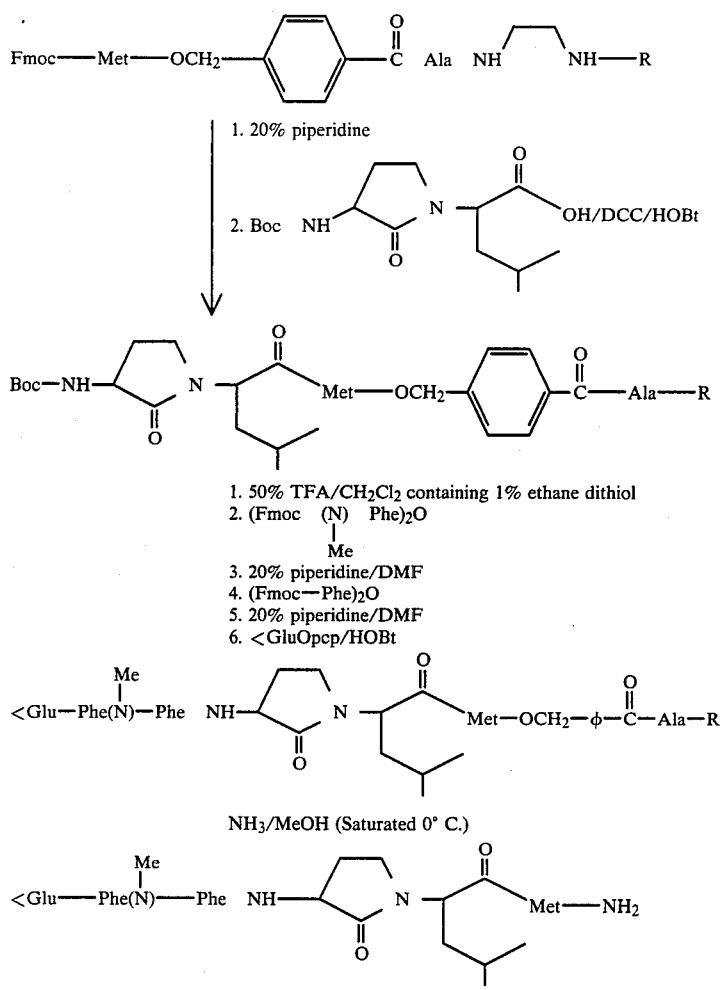

In the foregoing reaction scheme: Fmoc=b 9-fluorenylmethyloxycarbonyl, DMAP=dimethylaminopyridine, NMM=N-methylmorpholine, DCC=dicyclohexylcarbodiimide, HOBt=1-hydroxybenzotriazole, TFA=trifluoroacetic acid, pcp=pentachlorophenyl.

Employing similar techniques, there was prepared pyroglutamyl-glutaminyl-phenylalanyl-N-methyl-phenlalanyl [(R)-3-amino-2-oxo-1-pyrrolidinyl-(S)-4-methyl-2-pentanoyl]-methionine amide, which was characterized by mass spectrum, hplc, amino acid analysis and n.m.r.

Representative compounds of this invention were tested in the substance P (SP) and eledoisin binding assays. The peptides were dissolved in DMSO and tested for their abilities to compete for $^{125}$I-BH-SP and $^{125}$I-BH-eledoison binding sites in rat brain cortex membranes (Cascieri and Liang, *J. Biol. Chem.*, 258, 5158 (1983); *Life Sciences*, 35, 179 (1984)).

The following table summarizes the IC$_{50}$ data obtained in both assay systems as well as showing the IC$_{50}$ ratio for each peptide in the SP and eledoisin binding assays.

| | Binding Assays IC$_{50}$(M) | | IC$_{50}$SP/ |
|---|---|---|---|
| Compound | $^{125}$I-BH-eledoisin | $^{125}$I-BH-SP | eledoisin |
| L-363,851 | 1.4 × 10$^{-8}$ | 1.3 × 10$^{-5}$ | 929 |
| L-653,547 | 1.5 × 10$^{-7}$ | 1.4 × 10$^{-4}$ | 933 |
| L-653,561 | 4.5 × 10$^{-8}$ | 1.1 × 10$^{-4}$ | 2444 |
| L-653,562 | 1.8 × 10$^{-7}$ | 6.2 × 10$^{-5}$ | 344 |
| L-653,564 | 7.2 × 10$^{-8}$ | 1.2 × 10$^{-4}$ | 1667 |
| L-653,563 | 1.5 × 10$^{-7}$ | 8.4 × 10$^{-5}$ | 560 |
| L-363,232 | 3.2 × 10$^{-5}$ | 6.0 × 10$^{-5}$ | — |

EXAMPLE 3

The following examples of ophthalmic formulations are given by way of illustration.

| | | |
|---|---|---|
| L-363,851 | 1 mg. | 15 mg. |
| Monobasic sodium phosphate.2H$_2$O | 9.38 mg. | 6.10 mg. |
| Dibasic sodium phosphate.12H$_2$O | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phosphate buffer salts, and benzalkonium chloride are added to and dissolved in water. The pH of the composition is adjusted to 6.8 and diluted to volume. The composition is rendered sterile by ionizing radiation.

EXAMPLE 4

| L-653,547 (II) | 5 mg. |
|---|---|
| petrolatum q.s. ad. | 1 gram |

Compound II and the petrolatum are aseptically combined.

EXAMPLE 5

| L-653,561 | 1 mg. |
|---|---|
| Hydroxypropyl cellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R. H. at 30° C.) for two to four days. After removal from the humidity cabinet, the vials are stoppered and then capped. The vials containing the hydrate insert are then autoclaved at 250° F. for ½ hour.

EXAMPLE 6

| L-653,562 | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 7

| L-653,562 | 1 mg. |
|---|---|
| Hydroxypropylmethyl cellulose q.s. ad. | 12 mg. |

Ophthalmic inserts are manufactured from a solvent cast film which is prepared by making a viscous solution of the powered blend of the above ingredients using a methanol/water solvent system (10 ml. methanol is added to 2.5 g of the powdered blend, to which 11 ml of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 8

| L-653,564 | 1 mg. |
|---|---|
| Hydroxypropylmethyl cellulose q.s. ad. | 12 mg |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

EXAMPLE 9

| Solution Composition | |
|---|---|
| L-363,851 | 0.1 mg. |
| Peanut oil q.s. ad. | 0.10 mg. |

The solution is rendered sterile by filtration through a sterilizing filter.

EXAMPLE 10

| L-653,547 | 0.5 gm. |
|---|---|
| Petrolatum q.s. ad. | 1 gram |

The compound and the petrolatum are aseptically combined.

What is claimed:

1. A compound of structural formula:

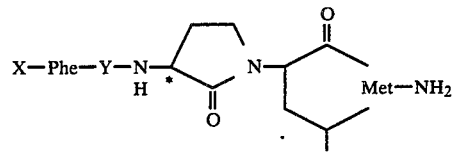

wherein
X is <Glu, <Glu-Gln, Ac-Ala, Ac-Phe, or Ac; and
Y is Phe, N-Me-Phe, Ile, Val or Tyr.

2. The compound of claim 1 wherein X is <Glu.
3. The compound of claim 1 wherein Y is Phe, Ile or Val.
4. The compound of claim 3 which is:

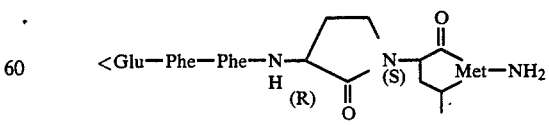

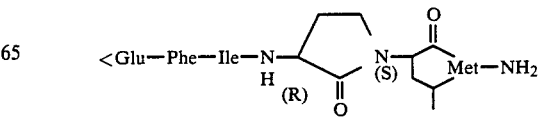

-continued

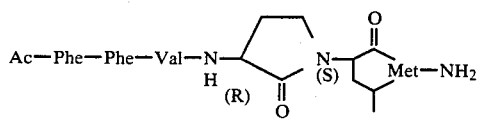

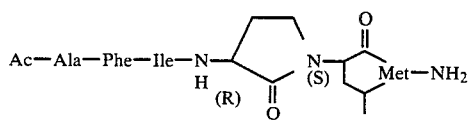

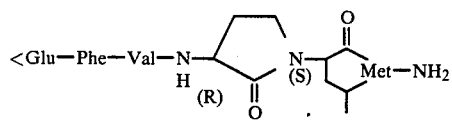

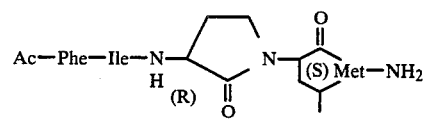

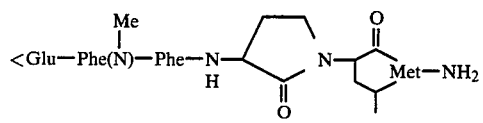

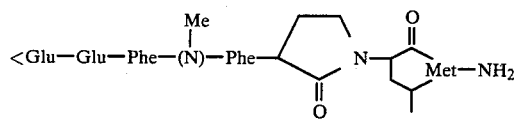

5. An ophthalmic composition for stimulating lachrymal secretion which comprises an ophthalmologically acceptable carrier and an effective lachrymal secretion stimulatory amount of a compound of structural formula:

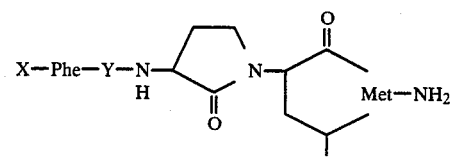

wherein X is <Glu, <Glu-Gln, Ac-Ala, or Ac-Phe, or Ac; and Y is Phe, N-Me-Phe, Ile, Val or Tyr.

6. The formulation of claim 5 wherein X is Glu.
7. The formulation of claim 5 wherein Y is Phe, Ile, or Val.
8. The formulation of claim 7 wherein the compound is:

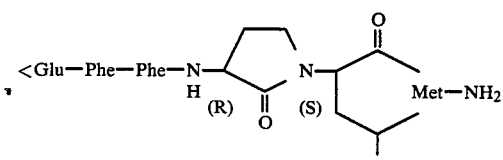

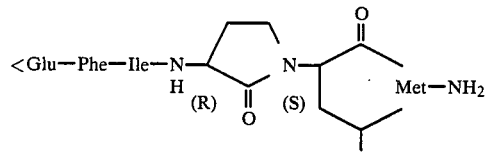

-continued

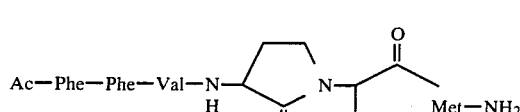

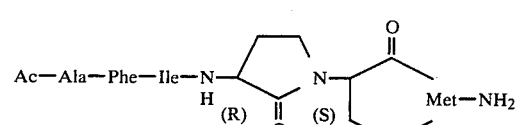

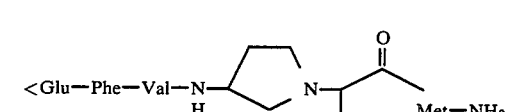

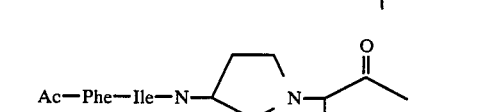

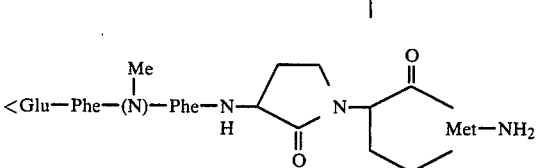

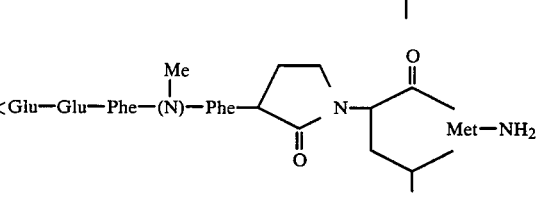

9. A method of stimulating lachrymal secretion in a patient in need of such treatment which comprises the administration of an effective amount of a compound of structural formula:

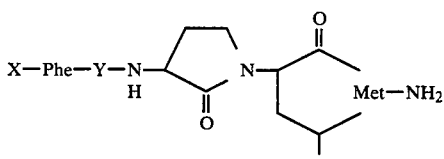

wherein X is <Glu, <Glu-Gln, Ac-Ala, or Ac-Phe, or Ac; and Y is Phe, N-Me-Phe, Ile, Val or Tyr.

10. The method of claim 9 wherein X is Glu.
11. The method of claim 9 wherein Y is Phe, Ile or Val.
12. The method of claim 11 wherein the compound is:

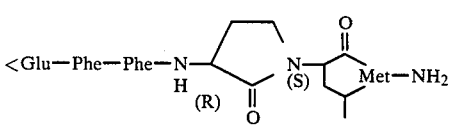

-continued
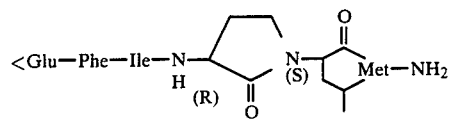
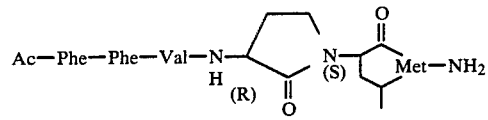
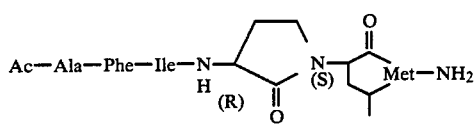
-continued
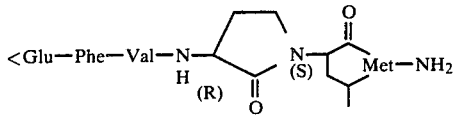
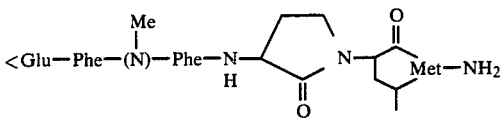
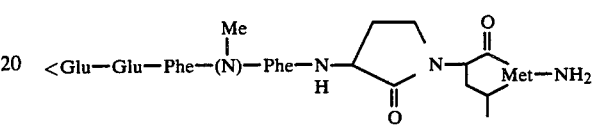
* * * * *